US007676257B2

(12) United States Patent
Suryanarayanan et al.

(10) Patent No.: US 7,676,257 B2
(45) Date of Patent: Mar. 9, 2010

(54) METHOD AND APPARATUS FOR SEGMENTING STRUCTURE IN CT ANGIOGRAPHY

(75) Inventors: Srikanth Suryanarayanan, Bangalore (IN); Rakesh Mullick, Bangalore (IN); Yogisha Mallya, Bangalore (IN); Vidya Pundalik Kamath, Bangalore (IN); Nithin Nagaraj, Bangalore (IN)

(73) Assignee: General Electric Company, Niskayuna, NY (US)

( * ) Notice: Subject to any disclaimer, the term of this patent is extended or adjusted under 35 U.S.C. 154(b) by 872 days.

(21) Appl. No.: 10/723,192

(22) Filed: Nov. 25, 2003

(65) Prior Publication Data

US 2005/0113679 A1    May 26, 2005

(51) Int. Cl.
*A61B 5/05* (2006.01)
*G06K 9/00* (2006.01)

(52) U.S. Cl. .................. 600/425; 382/128; 382/130
(58) Field of Classification Search .......... 600/425; 378/4, 21; 382/128, 130
See application file for complete search history.

(56) References Cited

U.S. PATENT DOCUMENTS

| 5,570,404 | A | 10/1996 | Liang et al. ............... 378/8 |
| 5,832,134 | A | 11/1998 | Avinash et al. ........... 382/257 |
| 6,351,571 | B1 * | 2/2002 | VanMetter et al. ....... 382/254 |
| 6,842,638 | B1 * | 1/2005 | Suri et al. .................. 600/425 |
| 7,432,924 | B2 * | 10/2008 | Ohishi ...................... 345/419 |

OTHER PUBLICATIONS

U.S. Appl. No. 10/301,018, filed Nov. 21, 2002, Mullick et al.

U.S. Appl. No. 10/304,581, filed Nov. 26, 2002, Suryanarayanan, Srikanth et al.

Adams, Rolf, et al., Seeded Region Growing, IEEE Transactions on Pattern Analysis and Machine Intelligence, vol. 16, No. 6, Jun. 1994, pp. 641-647.

Alyassin, Abdalmajeid M., et al., Semi-automatic Bone Removal Technique from CT Angiographic Data, Proceedings of the SPIE—The International Society for Optical Engineering 2000, General Electric Research & Development Center, GE Medical Systems.

Aylward, Stephen R., et al., Systems and Methods for Tubular Object Processing, PCT application, International Publication No. WO 01/78010 A2, IP Publication date Oct. 18, 2001.

(Continued)

*Primary Examiner*—Long V Le
*Assistant Examiner*—Jacqueline Cheng
(74) *Attorney, Agent, or Firm*—Jason K. Klindtworth

(57) ABSTRACT

A technique is provided for automatically generating a bone mask in CTA angiography. In accordance with the technique, an image data set may be pre-processed to accomplish a variety of function, such as removal of image data associated with the table, partitioning the volume into regionally consistent sub-volumes, computing structures edges based on gradients, and/or calculating seed points for subsequent region growing. The pre-processed data may then be automatically segmented for bone and vascular structure. The automatic vascular segmentation may be accomplished using constrained region growing in which the constraints are dynamically updated based upon local statistics of the image data. The vascular structure may be subtracted from the bone structure to generate a bone mask. The bone mask may in turn be subtracted from the image data set to generate a bone-free CTA volume for reconstruction of volume renderings.

38 Claims, 4 Drawing Sheets

OTHER PUBLICATIONS

Aylward, Stephen R., et al., Systems and Methods for Tubular Object Processing, PCT application, International Publication No. WO 01/78010 A3, IP Publication date Oct. 18, 2001.

Boehm, Guenther, et al., Three-Dimensional Segmentation of Bone Structures in CT Images, Proceedings of the SPIE, vol. 3661, p. 277-286, Medical Imaging 1999; Image Processing.

Cline, Harvey E., et al., Magnetic Resonance Segmentation with the Bubble Wave Algorithm, Proceedings of the SPIE, vol. 5032, pp. 1658-1666 (2003); Medical Imaging 2003; Image Processing.

Saha, Punam K. et al., Automatic bone-free rendering of cerebral aneurysms via 3D-CTA, Proceedings of the SPIE—The International Society for Optical Engineering, vol. 4322 n 3 2001, pp. 1264-1272.

Subramanyan, Krishna, Vessel Tracking and Tree Extraction Method and Apparatus, PCT application, International Publication No. WO 03/046835 A1, IP Publication date Jun. 5, 2003.

Venema, Henk W., et al., CT Angiography of the Circle of Willis and Intracranial Internal Carotid Arteries: Maximum Intensity Projection with Matched Mask Bone Elimination Feasibility Study, Radiology Mar. 2001, vol. 218(3), pp. 893-898.

Westin, Carl-Fredrik et al., Using Local 3D Structure for Segmentation of Bone from Computer Tomography Images, Proceedings of the IEEE Computer Society Conference on Computer Vision and Pattern Recognition 1997, IEEE, Los Alamitos, California, U.S.A., 97CB36082, p. 794-800.

Westin, C-F, et al., Tensor Controlled Local Structure Enhancement of CT Images for Bone Segmentation, Proc. Of First Int. Conf. On MICCAI, Springer, Verlag, pp. 1205-1212, 1998, Brigham and Women's Hospital, U.S.A.

Yan, Changjiang, et al., Extraction of Blood Vessel in CT Angiography Image Aided by Fuzzy Logic, Proceedings of ICSP2000, pp. 926-929.

* cited by examiner

METHOD AND APPARATUS FOR SEGMENTING STRUCTURE IN CT ANGIOGRAPHY

BACKGROUND OF THE INVENTION

The present invention relates generally to the field of medical imaging and particularly to the field of volumetric medical imaging. Specifically, the invention relates to a technique for segmenting bone and vasculature data in computed tomography.

Volumetric medical imaging technologies use a variety of techniques to gather three-dimensional information about the body. For example, computed tomography (CT) imaging system measure the attenuation of X-ray beams passed through a patient from numerous angles. Based upon these measurements, a computer is able to reconstruct images of the portions of a patient's body responsible for the radiation attenuation. As will be appreciated by those skilled in the art, these images are based upon separate examination of a series of angularly displaced cross sections. It should be pointed out that a CT system produces data that represent the distribution of linear attenuation coefficients of the scanned object. The data are then reconstructed to produce an image that is typically displayed on a cathode ray tube, and may be printed or reproduced on film.

For example, in the field of CT angiography (CTA), vasculature and other circulatory system structures may be imaged, typically by administration of a radio-opaque dye prior to imaging. Visualization of the CTA data typically is performed in a two-dimensional manner, i.e., slice-by-slice, or in a three-dimensional manner, i.e., volume visualization, which allows the data to be analyzed for vascular pathologies. For example, the data may be analyzed for aneurysms, vascular calcification, renal donor assessment, stent placement, vascular blockage, and vascular evaluation for sizing and/or runoff. Once a pathology is located, quantitative assessments of the pathology may be made of the on the original two-dimensional slices.

The CTA process may include processes for segmenting structures in the image data, such as the vasculature and/or the bone structures. Such segmentation typically involves identifying which voxels of the image data are associated with a particular structure or structures of interest. Segmented structures may then be viewed outside of the context of the remainder of the image data or may be masked from the remainder of the image data to allow otherwise obstructed structure to be viewed. For example, in CTA, segmentation may be performed to identify all voxels associated with the vasculature, allowing the entire circulatory system in the imaged region to be extracted and viewed. Similarly, all voxels of the bone structures may be identified and masked, or subtracted, from the image data, allowing vasculature and/or other structures which might otherwise be obscured by the relatively opaque bone structures to be observed during subsequent visualization.

However, segmentation of vasculature and bone structures may be complicated by a variety of factors. For example, in CTA, overlapping image intensities, close proximity of imaged structures, limited detector resolution, calcification, and interventional devices may make the identification and segmentation of bone and vascular structures difficult. Furthermore, anatomic regions and sub-regions of complex anatomy within the imaging volume may benefit from differential processing techniques. In particular, the complex landscape of the bone and vasculature in the head and neck region, may benefit from differential processing based on distinct sub-regions within the overall regions.

Because of these complicating factors, existing segmentation techniques may improperly exclude image data from the segmented structure due to poor edge recognition and/or non-homogeneities in the image data. Such exclusions may potentially result in early or erroneous termination of the segmentation technique. Furthermore, splits or mergers in the structure of interest may not be properly segmented by existing techniques due to these shortcomings. Alternatively, overlapping intensity ranges and/or poor edge recognition may result in the improper inclusion of proximate background regions in the segmented structure, leading to late termination of the segmentation process.

As a result, proper segmentation of a complex or contiguous three-dimensional structure, such as the vasculature around the head and neck region, may require operator intervention or input. In particular, operator intervention may be needed to designate initial start points and/or to prevent the inadvertent inclusion or exclusions of volume data from the segmented structure. For example, the operator may manually remove bone by drawing contours around bone on a few slices and building up the bone structure to be removed. Based on the results, the operator may repeat this process for the slices in question until a satisfactory result in achieved, at which time the operator may proceed to the next set of slices to be iteratively processed in this manner. This process may be particularly difficult in the head and neck region due to the poor bone boundaries observed via CT and other imaging modalities. Furthermore, the shape of the bone may change rapidly in the space of a few slices, preventing the operator from using the same contour as an initial reference in more than a few slices. As a result, the operator may have to redraw or reset the contour repeatedly throughout the process, potentially taking over an hour to process an imaged head and neck volume. In addition, the operator intervention may lead to inter- and intra-user variability in the segmentation of structures.

Due to the labor intensiveness of this process, the operator may attempt to reduce the processing time by limiting the process to a region or volume of interest corresponding to the location of the pathology. Limiting the process in this manner, however, does not take full advantage of the entire set of volume data available. Furthermore, limiting the processing to the known or suspected region of a pathology may prevent additional pathologies which are obscured from being discovered, despite the availability of the data. It may, therefore, be desirable to automate the process for segmentation, extraction and masking of structure in the CTA process for complex anatomic regions, such as the head and neck.

BRIEF DESCRIPTION OF THE INVENTION

The present technique provides a novel approach to automatically generate a bone mask from CTA data. In particular, the technique may be useful for automatically generating a bone mask of the head and neck region. According to the present technique, an image data set may be pre-processed to facilitate segmentation of the structures of interest, usually bone and vasculature. Pre-processing of the data may involve removing image data associated with the table or support, partitioning the volume data into sub-volumes, which reflect local anatomy, computing gradients indicative of structure edges, and/or calculating seed points which may be used during segmentation. During the segmentation process, bone may be aggressively segmented, such as based on intensity. Vasculature may be automatically segmented based on a variety of techniques, including dynamic constrained region growing, bubble wave connectivity, and/or ray and contour propagation. The vasculature may be smoothed after segmentation if desired. The vasculature may be subtracted from the segmented bone to generate a bone mask, which may in turn be subtracted from the image data to generate a bone-free date set. The bone-free data set may be reconstructed or rendered to produce a bone-free volume for viewing.

In accordance with one aspect of the present technique, a method for generating a bone mask is provided. As provided by this aspect, an image data set is acquired and pre-processes to automatically calculate at least one or more seed points and one or more structure edges. A preliminary bone mask is generated from the image data set. A vascular structure is automatically determined using the one or more seed points, the one or more structure edges, and the image data. The vascular structure is subtracted from the preliminary bone mask to generate a bone mask. Systems and computer programs that afford functionality of the type defined by this method are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
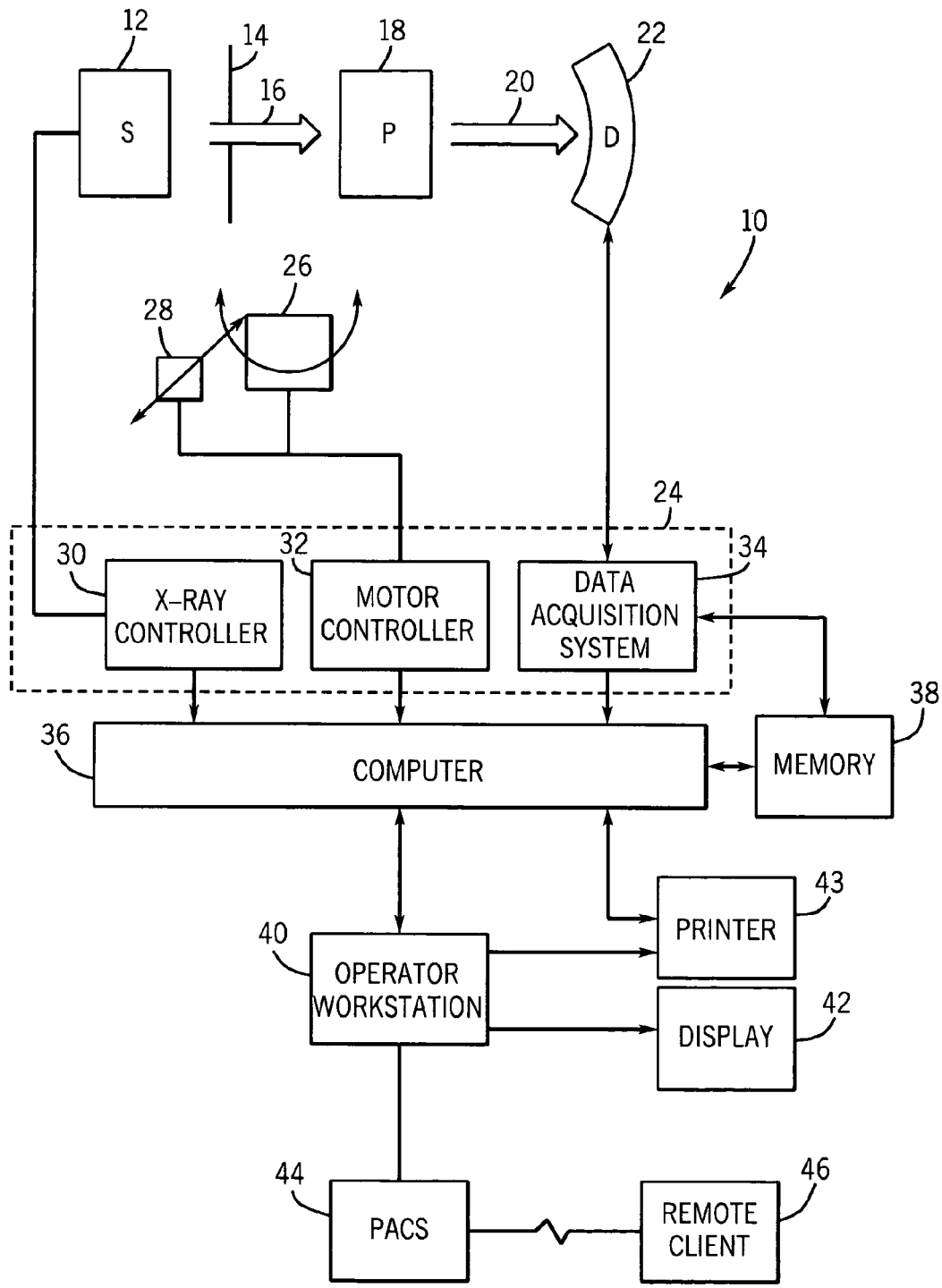
FIG. 1 is a diagrammatical view of an exemplary imaging system in the form of a CT imaging system for use in producing processed images in accordance with aspects of the present technique.

FIG. 1 illustrates diagrammatically an imaging system 10 for acquiring and processing image data. In the illustrated embodiment, system 10 is a computed tomography (CT) system designed both to acquire original image data and to process the image data for display and analysis in accordance with the present technique. Other imaging modalities which acquire image data for a volume, such as magnetic resonance imaging (MRI) or positron emission tomography (PET), may also benefit from the present techniques. The following discussion of CT systems is merely an example of one such implementation and is not intended to be limiting in terms of modality or anatomy.

In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube. Collimator 14 permits a stream of radiation 16 to pass into a region in which a subject, such as a human patient 18 is positioned. A portion of the radiation 20 passes through or around the subject and impacts a detector array, represented generally at reference numeral 22. Detector elements of the array produce electrical signals that represent the intensity of the incident X-ray beam. These signals may be acquired and processed to reconstruct an image of the features within the subject.

Source 12 is controlled by a system controller 24 that furnishes both power and control signals for CT examination sequences. Moreover, detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, interface circuits, and so forth. The system controller 24 may also include associated memory circuitry for storing configuration parameters, image data, and/or programs and routines executed by the computer. For example, programs and routines implementing the present technique, in whole or in part, may be stored on memory circuitry accessible to the system controller 24, such as on one or more optical and/or magnetic media.

In the embodiment illustrated in FIG. 1, system controller 24 is coupled to a rotational subsystem 26 and linear positioning subsystem 28. The rotational subsystem 26 enables the X-ray source 12, collimator 14 and the detector 22 to be rotated one or multiple turns around the patient 18. It should be noted that the rotational subsystem 26 may include a gantry. Thus, the system controller 24 may be utilized to operate the gantry. The linear positioning subsystem 28 enables the patient 18, or more specifically a patient table, to be displaced linearly. Thus, the patient table may be linearly moved within the gantry to generate images of particular areas of the patient 18. A motor controller 32 may be utilized to control the movement of the rotational subsystem 26 and the linear positioning subsystem 28. Additionally, the source of radiation may be controlled by an X-ray controller 30 disposed within the system controller 24. Particularly, the X-ray controller 30 is configured to provide power and timing signals to the X-ray source 12.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing and/or display by a computer 36.

The computer 36 is typically coupled to the system controller 24. The data collected by the data acquisition system 34 may be transmitted to the computer 36 and moreover, to a memory 38. It should be understood that any type of memory to store a large amount of data may be utilized by such an exemplary system 10. Also the computer 36 is configured to receive commands and scanning parameters from an operator via an operator workstation 40 typically equipped with a keyboard and other input devices. An operator may control the system 10 via the input devices. A display 42 coupled to the operator workstation 40 may be utilized to observe the reconstructed image and to control imaging. Additionally, the scanned image may also be printed on to a printer 43 which may be coupled to the computer 36 and the operator workstation 40. Thus, the operator may observe the reconstructed image and other data relevant to the system from computer 36, initiate imaging, and so forth.

Further, the operator workstation 40 may also be coupled to a picture archiving and communications system (PACS) 44. It should be noted that PACS 44 may be coupled to a remote system 46, radiology department information system (RIS), hospital information system (HIS) or to an internal or external network, so that others at different locations may gain access to the image and to the image data.

It should be further noted that the computer 36 and operator workstation 46 may be coupled to other output devices that may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
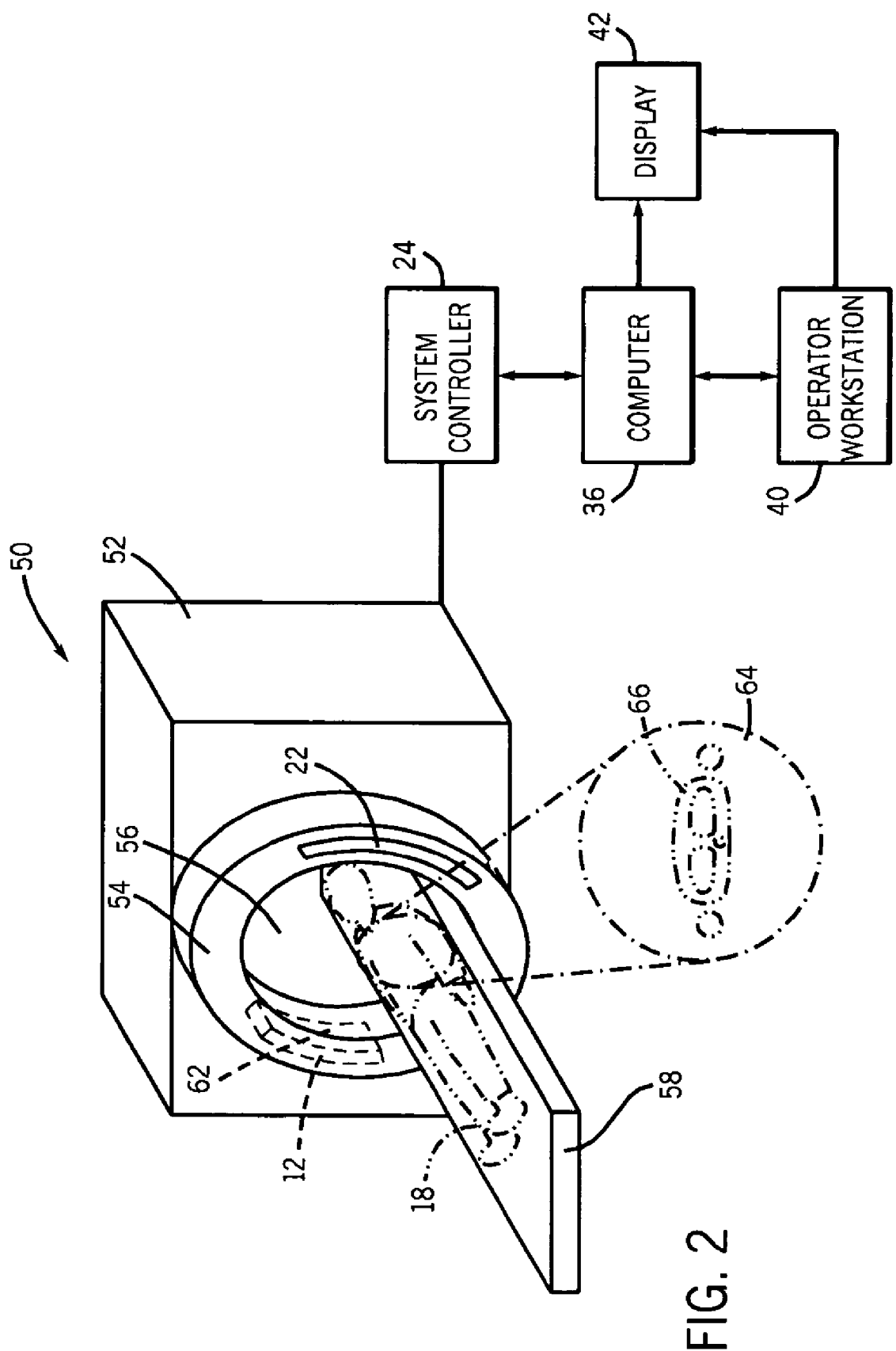
FIG. 2 is another diagrammatical view of a physical implementation of the CT system of FIG. 1.

Referring generally to FIG. 2, an exemplary imaging system utilized in a present embodiment may be a CT scanning system 50. The CT scanning system 50 is illustrated with a frame 52 and a gantry 54 that has an aperture 56. The aperture 56 may typically be 60 cm to 70 cm in diameter. Further, a patient table 58 is illustrated positioned in the aperture 56 of the frame 52 and the gantry 54. The patient table 58 is adapted so that a patient 18 may recline during the examination process. Additionally, the patient table 58 may be configured to be displaced linearly by the linear positioning subsystem 28 (see FIG. 1). The gantry 54 is illustrated with the source of radiation 12, typically an X-ray tube, which emits X-ray radiation from a focal point 62. The stream of radiation is directed towards a particular region of the patient 18. It should be noted that the particular region of the patient 18 is typically chosen by an operator so that the most useful scan of a region may be acquired. As mentioned above, the computer 36 is typically used to control the entire CT system 10. The main computer that controls the operation of the system may be adapted to control features enabled by the system controller 24. Further, the operator workstation 40 is coupled to the computer 36 as well as to a display, so that the reconstructed image may be viewed.

In typical operation, X-ray source 12 projects an X-ray beam from the focal point 62 and toward detector array 22. The detector 22 is generally formed by a plurality of detector elements that sense the X-rays that pass through and around a region of interest, such as particular body parts. Each detector element produces an electrical signal that represents the intensity of the X-ray beam at the position of the element at the time the beam strikes the detector. Furthermore, the gantry 54 is rotated around the subject of interest so that a plurality of radiographic views may be collected by the computer 36. Thus, an image or slice is acquired which may incorporate, in certain modes, less or more than 360 degrees of projection data, to formulate an image. The image is collimated to a desired thickness, typically between 0.5 mm and 10 mm using either lead shutters in front of the X-ray source 12 and different detector apertures 22. The collimator 14 (see FIG. 1) typically defines the size and shape of the X-ray beam that emerges from the X-ray source 12.

Thus, as the X-ray source 12 and the detector 22 rotate, the detector 22 collects data of the attenuated X-ray beams. Data collected from the detector 22 then undergoes pre-processing and calibration to condition the data to represent the line integrals of the attenuation coefficients of the scanned objects. The processed data, commonly called projections, are then filtered and backprojected to formulate an image of the scanned area.

Once reconstructed, the image produced by the system of FIGS. 1 and 2 reveals internal features of a patient. As illustrated generally in FIG. 2, an image slice 64 of the reconstructed volume or the reconstructed volume itself may be displayed to show these features, such as indicated at reference numeral 66 in FIG. 2. In diagnosing medical conditions, such as disease states, and more generally of medical events, a radiologist or physician may consider a hard copy of display of the image 64 to discern characteristic features of interest. Such features might include lesions, sizes and shapes of particular anatomies or organs, and other features that would be discernable in the image based upon the skill and knowledge of the individual practitioner. Other analyses may be based upon capabilities of various CAD algorithms. As will be appreciated by those skilled in the art, CAD algorithms may offer the potential for identifying, or at least localizing, certain features of interest, such as anatomical anomalies. Subsequent processing and data acquisition may then be determined at the discretion of and based upon the expertise of the practitioner.

Though a two-dimensional axial slice is depicted as image 64 is depicted in FIG. 2, in practice image 64 may also be a volumetric rendering, such as a volume and/or surface rendering. These volumetric rendering techniques allow three-dimensional visualization by the operator and may provide more information than simply scanning two-dimensional axial slices. However, when CTA data is rendered volumetrically, bone structure may form an occluding barrier that needs to be segmented and masked out. Furthermore, in CTA it may be desirable to segment and extract the vasculature from the remainder of the background. However, the segmentation process may be complicated by overlapping image intensities of bone (trabecular and cortical) and contrast-enhanced vessels. In addition, in complex anatomical region, such as the head/neck region, the complex anatomical landscape and the spatial relationship between bone and vessel may complicate segmentation, particularly in an automated context. As a result, prohibitively time-consuming operator assistance may be involved in the generation of CTA volumetric renderings involving segmentation and extraction or masking of structure.

Figure 3:
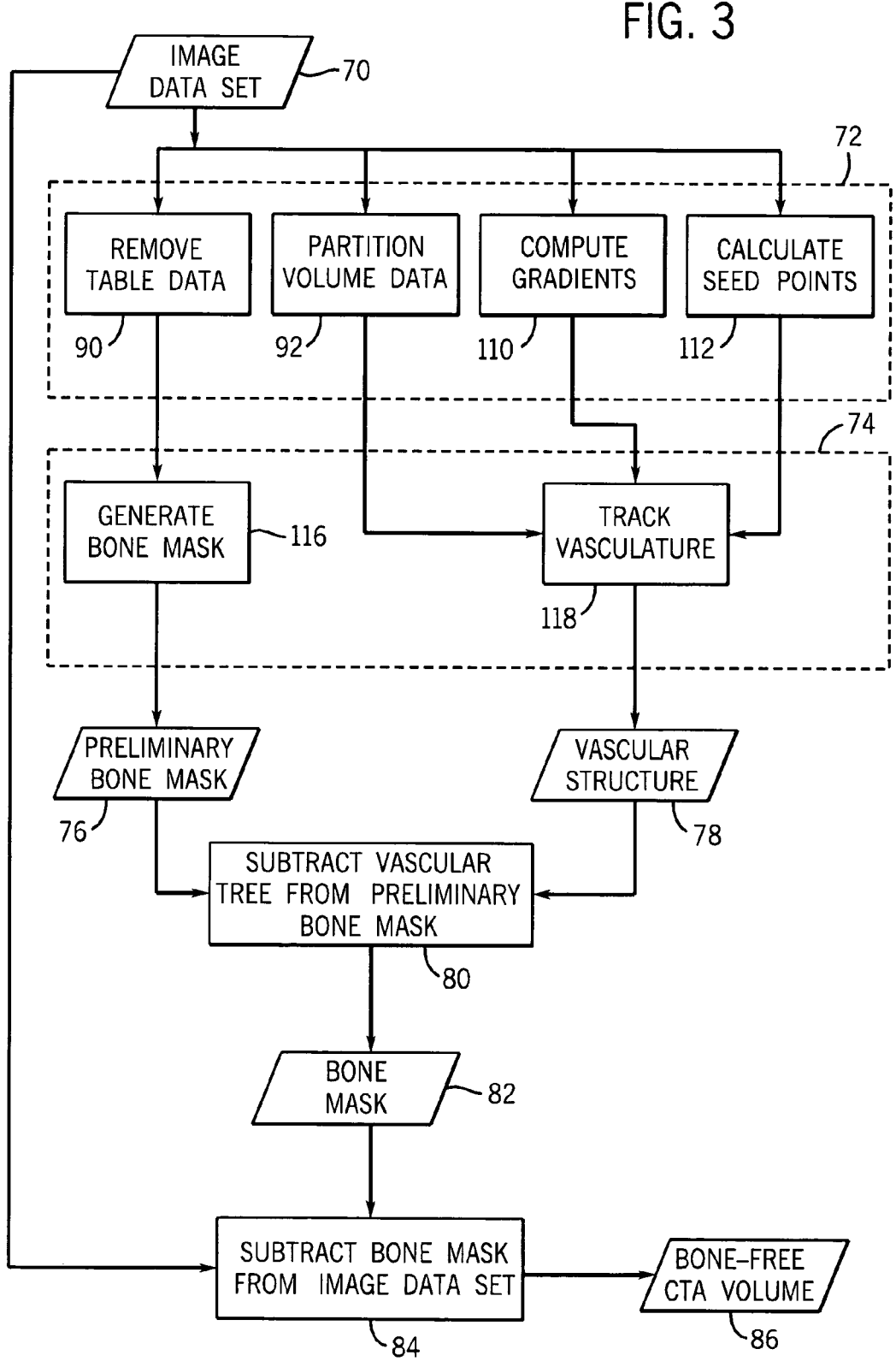
FIG. 3 is a flowchart depicting aspects of the present technique.

A technique to facilitate automation of volumetric image processing is depicted and discussed with regard to FIG. 3 and subsequent figures. As depicted in FIG. 3, the image data set 70, typically a stack of 512×512 axial slices stored as a DICOM series, may be pre-processed at step 72 prior to structure segmentation at step 74. As depicted, both the pre-processing step and'structure segmentation step may include various sub-steps. The structure segmentation step 74 generally results in a preliminary bone mask 76 as well as a vascular tree 78. The vascular tree 78 may be subtracted from the preliminary bone mask 76 at step 80 to generate a bone mask 82. The bone mask 82 may be subtracted from the image data set 70 at step 84 to generate a bone-free CTA volume 86 which may be rendered as a three-dimensional construct for review and analysis by a radiologist or technologist. By the present technique, the various steps performed on the image data set 70 to generate the bone-free CTA volume may be automated and performed in a computationally efficient manner.

As noted above, the image data set 70 acquired during CTA may be pre-processed at step 72 by a number of possible sub-steps. For example, the image data associated with the table or support may be removed from further processing, as depicted at step 90. Table removal may be accomplished by estimating gray level for the regions of the image volume associated with the table and the patient. These estimates may then be used to locate the general areas in the imaged volume occupied by these two distinct bodies. Connected component analysis or a similar analytical technique may be used to narrow down the regions into contiguous blocks of image data. Contours of the regions determined to belong to the patient data are extracted and the interior of each contour is completely filled to form a mask for the area. The mask may be used to retain original data from the image data set 70 while all data exterior to the mask may be suppressed from further processing, thereby eliminating the table data from subsequent processing of the image data set 70.

In addition, a partitioning sub-step 92 may be performed on the image data set 70. For example, the vascular structures in the head and neck region follow a tortuous path from the neck to the brain. Within the head and neck region, defined distally by the aortic arch where the common carotid arteries branch out and proximally by the top of the skull, various sub-volumes may be identified which vary in their degree of spatial separation between bone and vessel.

For example, the most complex portion is the skull base region and a topological network called the Circle of Willis formed by multiple arteries which arrive distally from the neck to form the circular network. Several smaller arteries emerge from this circle to supply blood to the various parts of the brain. To complicate matters with regard to CTA, this region is partially embedded in bone. The bone structure is also very complex resembling a thin hollow shell that makes the bone boundaries appear fuzzy when imaged. Specific to the head and neck anatomy is also the vertebral artery that travels along the cervical vertebrae embedded in the transverse foramen. The size and location of this artery makes manual editing problematic. These complexities make CTA of the head and neck region difficult but also highlight the presence of local sub-volumes within the imaged volume that may benefit from differential processing adapted to address the specific complexities of the sub-volumes.

In particular, partitioning may reflect the degree of spatial separation in a local anatomic region. Sub-volumes in which the spatial separation between bone and vessel is good may allow greater emphasis on techniques such as connected components to distinguish between bone and vessel structures. However, sub-volumes which have poor spatial separation between bone and vessel, may benefit from more complex model driven techniques to differentiate the bone and vessels. The partitioning step 92 may, therefore, partition the imaged volume by analyzing its landscape such that the sub-volumes have consistent separation between the objects of interest.

For example, the head and neck region may be partitioned into three sub-volumes. The distal sub-volume may extend from the aortic arch to the distal end of the petrous segment, i.e., the edge of the skull base. In this sub-volume, the carotids are spatially well separated from the bone regions. The middle sub-volume comprises the petrous segment, skull-base, and the Circle of Willis. Bone and vessel may appear contiguous in the middle sub-volume due to the similarity of intensity and close spatial locations. In particular, the bone forms a thin hollow shell like structure in the skull base that, in axial slices, possesses fuzzy boundaries that may be difficult to identify. At the proximal end of the middle sub-volume is the Circle of Willis which is oriented obliquely in 3-D and partially embedded in bone. The arterial junctions are popular sites for the formation of small berry like aneurysms. Proximal to the Circle of Willis lays the proximal sub-volume that comprises the cranial region. In this region, the skullcap is the only bone structure and is well separated spatially from the cerebral arteries.

Based on the above anatomical considerations, the partition step 92 may compute and place partition lines to create three sub-volumes. This may be achieved by the use of energy profiles. In this context, the energy of an image is a measure of a selected feature. For CT applications, it is generally desirable to choose bone or air gaps, i.e., the sinuses, since they have distinct and consistent intensity patterns. The bone and sinus profile may be generated for the entire volume by accumulating all voxels classified as belonging to bone or sinus region in each axial slice. Alternatively, a parallel definition of energy in an image comes from the classical theories of entropy. The first order distribution of intensities in an image becomes a measure of how "busy" or "quiet" an image is. The entropy profile may then be generated by computing the first order distribution of voxels classified as belonging to bone and vascular regions.

Figure 4:
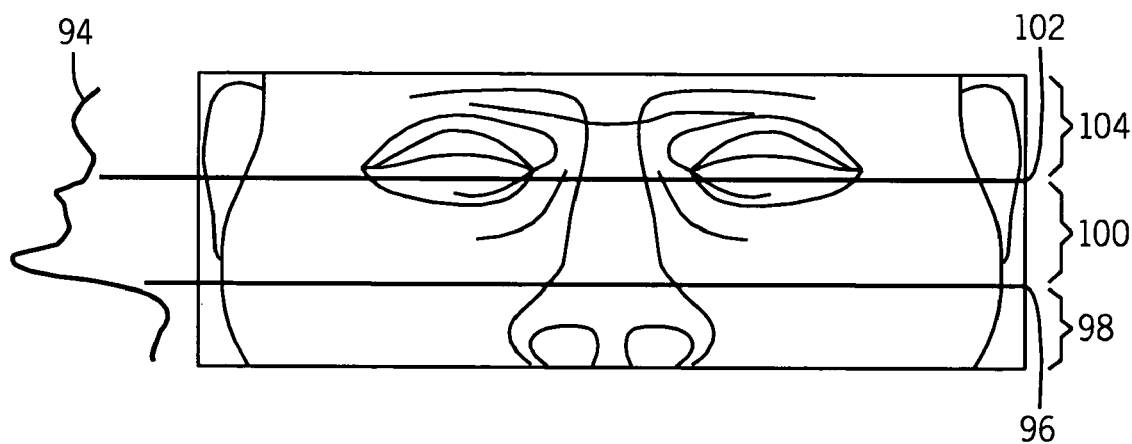
FIG. 4 is a coronal view of a head with partition lines subdividing the head into three sub-volumes in accordance with an exemplary bone profile.

The partition lines may be computed by a rule-based method. The rule-based method may search the profiles and identifies the sub-volume slices that correlate to the visually identified partition lines. For example, referring to FIG. 4, a coronal view of a head is depicted with partition lines subdividing the head into the three sub-volumes in accordance with an exemplary bone profile 94. A first partition line 96, located based upon the bone profile 94, separates the distal sub-volume 98 and the middle sub-volume 100. A second partition line 102 separates the middle sub-volume 100 and the proximal sub-volume 104. Within each sub-volume, suitable differential processing may be employed to segment the bone and vasculature based upon the consistent spatial relationship of the bone and vasculature in the sub-volume. For example, the spatial separation between bone and vessel in the proximal sub-volume may be exploited to implement a much faster routine to extract bone and vessel. Similarly, the vessel tracking techniques, discussed in greater detail below, may be restricted to a sub-volume rather than to the entire data set. For example, a data set of size 512×512×175 may be processed in 35 seconds (0.2 seconds per slice), because the partitions calculated (in this case, slices 29 and 91 of the volume) allow a fast algorithm to be implemented in the slice range 91-175 (84 slices) and the more complex vessel tracking algorithm is applied only in the 29-91 (62 slices) slice range.

In addition to removing table data and partitioning the image data, gradients may be computed in the image data at sub-step 110 of the pre-processing step 72. The gradients may be used to determine structure boundaries, which may be marked by sharp changes of intensity. One method of identifying the transition location is by the use of gradient and edge maps. The gradient for each voxel of the imaged volume may be computed by finding maximum absolute gradient component in its neighborhood. For example, for an interior voxel, the maximum absolute gradient between that voxel and the twenty-six adjacent voxels may be computed. This gradient computation forms a strong boundary around the various objects in the dataset even in the presence of noisy boundaries. The maximum absolute gradient associated with each voxel may be used to generate a gradient map to facilitate edge detection. In particular, the robust edge protection may prevent the inadvertent crossing of structure edges and boundaries by subsequent region growing processes.

The pre-processing step 72 may also include a sub-step 112 for calculating seed points that correspond to regions of vasculature or other three-dimensional structures in the image data set 70. The seed points may then be utilized as starting points for identifying the respective structure or vasculature via a constrained growing process. Seed points may be represented or identified by using simple and rudimentary two-dimensional or three-dimensional geometric templates. Customized template models can be created for objects of interest depending on the application. In particular, cross-section or projection data of three-dimensional objects can be used to generate template models.

For example, in CTA, the object of interest is typically vessels that are three-dimensional tubular or cylindrical structures. As a result, the cross-sections of the main blood vessels are generally circular in nature either in axial, coronal, sagittal, or an arbitrary oblique plane in the image data set 70. Therefore, a simple template model that may be used to identify vessels is a cross-sectional "round" region.

Similarly, functional or behavioral features may also be captured as templates to identify objects of interest. For example, a functional template model for CTA may be defined using statistical homogeneity criteria. Such a template model may exploit a functional property, such as uniform x-ray attenuation, of contrast agents flowing continuously through the blood vessel during the CT scan. In this example, a cross-section corresponding to main blood vessels in the image data set 70 may be automatically located by detecting round regions with low standard deviation of intensities. For example, in an exemplary CTA application using both geometric and functional templates, a threshold of 76 HU may be used to suppress all soft tissues in the image data set 70. A low standard deviation of value 70 may be used to eliminate any round regions corresponding to bone. The resulting detected round regions may be used as seed areas for subsequent constrained region growing.

While the preceding discussion relates some possible sub-steps that may be performed during the pre-processing step 72, other sub-steps may also be performed, such as edge-sharpening or blurring routines, data filtering, and so forth. Similarly, while an exemplary CTA application may include the preceding sub-steps discussed with regard to the pre-processing step 72, one or more of the preceding sub-steps may be omitted if desired or if a suitable alternative is available.

Subsequent to whatever pre-processing is performed at step 72, the pre-processed data may be segmented at step 74. For example, in the CTA context, both bone and vasculature may be segmented for subsequent processing and to allow visualization of diagnostically useful volumes. With regard to bone segmentation, a preliminary bone mask 76 may be generated at step 116. In the exemplary discussion, the step 116 of generating the bone mask is performed on image data from which the table data has been removed or masked at step 90, as previously discussed. As noted above, however, the step of removing the table image data may be omitted in some instances.

The generation of the preliminary bone mask 76 at step 116 identifies all likely bone voxels in the head and neck, or other, volume. Identification of bone in the head and neck region is challenging due to the complex anatomical structure and the large intensity range associated with cortical and trabecular bone. Further, models used to identify bone in other parts of the body are not generally useful for identifying bone in the head and neck region due to anatomical difference between the bones of the skull and other bones of the body. In CTA the situation aggravated by the contrast-enhanced vessels passing through the thin bone of the skull base, which makes them appear contiguous.

Simple intensity and region-based methods may be used to aggressively identify all likely bone voxels in the head and neck volume as bone. Aggressive classification approaches insure inclusion of partial volume average and thin cortical regions as well as weak trabecular and sinus bones in the preliminary bone mask 76. If aggressive inclusion is employed, however, the bone mask generation algorithm may also include some vascular structures as bone. As will be discussed below, these vascular structures may be subtracted from the preliminary bone mask 76 to generate a true bone mask 82.

Identification of the vasculature structure 78 may be accomplished using one or more vascular tracking techniques, as depicted at step 118. Various techniques may be employed for vessel tracking at step 118, such as dynamic constrained region growing, bubble wave connectivity, and/or ray and contour propagation. For example, dynamic constrained region growing may be employed to track and grow the vascular structure 78 or other three-dimensional structure of interest. Dynamic constrained region growing may perform automatic initialization during which starting points for dynamic path finding are computed. These starting points may be obtained from the template-based seed point calculation step 72. The region edges, as determined from the gradient computed at step 110, may form a boundary that prevents the tracking from expanding to adjacent structures and background regions, i.e., the region edges constrain the growth process. Based on these constraints and starting points, dynamic path finding may be performed to extract the three-dimensional structures of interest, such as the vascular structure 78. The tracking constraints under which candidate voxels are selected to merge into the growing structure may be dynamically altered based upon local statistics, such as local intensity and/or homogeneity measures and/or variation. Furthermore, the constraints may be dynamically altered based upon the sub-volume associated with the voxels under consideration, i.e., the sub-volume may determine the constraints or the manner in which the constraints are modified in view of the local statistics.

Alternatively, bubble wave propagation may be employed for vessel tracking to determine the vascular structure 78. In bubble wave propagation, a dynamic bubble is passed through the three-dimensional structure to identify all the voxels belonging to the region. The bubble must find local volume through which it can pass. This criterion prevents the bubble from selecting voxels from adjacent objects that may be connected through weak bridges or from selecting background voxels. The size of the bubble is varied dynamically to adapt to the size of the object. At each iteration, the bubble grows by including voxels in a local neighborhood based on homogeneity criterion. The bubble wave is iteratively propagated first in a forward direction and then in a backward direction to exhaustively search the path of the object. The size and shape of the bubble can be customized for the object of interest and the application, such as from vessel tracking in CTA.

In addition, contour and ray propagation may be employed for vessel tracking to determine the vascular structure 78. Contour and ray propagation is based on the observations that blood vessels are mostly continuous and statistically homogeneous and consistent across adjacent slices and that blood vessels appear to be nearly circular in cross-section when viewed from a point within the vessel along the plane of the medial axis. The initial structure contour may be obtained manually or from the seed points calculated at step 72. This contour may be projected on to an adjacent slice in the default view. The total sum of squared intensities error is computed for the position of the contour at all points within a given window, such as a 30 x 30 window, and the contour is settled at the location where the error is a minimum. The centroid of the contour may then be computed and rays propagated from the centroid out of the contour. The number of rays can be set by the user beforehand. Likewise, the length of the rays may depend on the scale of the vessel and may also be set beforehand. A rules-based decision may then be made along each ray to determine the boundary point of the vessel. The rules may be constructed beforehand using models for vessel-to-soft-tissue and vessel-to-bone transitions. Once the boundary points are determined, this forms the new contour, which is then projected on to the next slice. Interactivity may be provided at this stage so that the user can change the axis of view for propagating the contour, which may be desirable at points where the vessel bends and is no longer circular in the current cross-section but would be circular in another three-dimensional plane. The medial axis along with the boundary of the vessel is readily available during and after the propagation process and may be used to make vessel measurements.

While the preceding processes may be used, for vessel tracking, other processes may also be used. Similarly, the above processes may be used alone or in conjunction with one another. The selection of or reliance placed upon a vessel tracking process may be determined based upon the image data set 70 or upon maps, sub-volumes, or regions determined during the pre-processing step 72.

Subsequent to determination of the preliminary bone mask 76 and the vascular structure 78, post-processing may be performed to eliminate partial volume averaging in voxels of the preliminary bone mask 76 and to smooth vascular structure 78 for improving the aesthetic quality of rendering. For example, the aggressive bone masking used to generate the preliminary bone mask 76 may include some vascular regions. To address this incidental inclusion, the vascular structure 78 may be subtracted from the preliminary bone mask 76 to generate the bone mask 82. However, conservative tracking of vessels at step 118 along with aggressive bone segmentation at step 116 may lead to vessels having irregular contours in the vascular structure 78. This irregularity may degrade the aesthetic quality of the three-dimensional visualization of the data. Three-dimensional smoothing may therefore be performed to improve the visualization quality. In particular, the contours between the planes may be interpolated to reduce the irregularity. Once generated in the desired form, the bone mask 82 may be subtracted from the image data set 70, as depicted at step 84, to generate a bone-free CTA volume 86. The bone-free CTA volume 86 may undergo a visualization process, such as a three-dimensional rendering technique, to generate a volume depiction from which the bone structures have been removed.

Because the present technique may be implemented as one or more automated routines, the labor and time intensiveness of manual processing may be avoided. Furthermore, the aggressive identification of bone combined with the conservative identification vasculature allow for the automatic generation of a true bone mask very quickly and without the tedious manual contour tracing typically associated with bone segmentation in complex regions, such as the head and neck. For example, the present technique, when implemented as one or more automated algorithms or routines, allows for the processing of an image slice in less one second and may allow for the processing of a slice in 0.3 seconds or less.

The speed with which the technique may perform, when implemented in an automated fashion, allows for easy integration into a clinical workflow. For example, the bone-free images and/or volumes that may be generated by the technique may be made promptly available to a radiologist for review. Comparatively, with manual segmentation and processing, bone-free images and volumes may be unavailable to the radiologist until after the radiologist has already reviewed the available image data and proceeded to the next case. As a result, clinical workflow can be enhanced, and the information available to the radiologist's increased, by means of the present technique.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for generating a bone mask, comprising the steps of:
   acquiring an image data set;
   pre-processing the image data set to automatically calculate at least one or more seed points and one or more structure edges;
   generating a preliminary bone mask to differentiate bone and vascular structures from the image data set, wherein the preliminary bone mask is generated for a plurality of sub-volumes comprising the image data set, each of the sub-volumes is identified based upon the degree of spatial separation between the bone and the vascular structures in the sub-volume, and wherein differential processing to segment the bone and vascular structures is employed within each sub-volume is based upon the spatial relationship between the bone and the vascular structures in the sub-volume;
   automatically determining the vascular structure using the one or more seed points, the one or more structure edges, and the image data; and
   subtracting the vascular structure from the preliminary bone mask to generate a bone mask.

2. The method as recited in claim 1, comprising the step of:
   subtracting the bone mask from the image data set to generate a bone-free volume data set.

3. The method as recited in claim 2, comprising the step of:
   rendering the bone-free volume data set to generate a bone-free volumetric rendering.

4. The method as recited in claim 1, wherein acquiring the image data set comprises acquiring a CTA data set of a head and neck region.

5. The method as recited in claim 1, wherein the step of pre-processing the image data set calculates the one or more seed points using at least one of a geometric template and a functional template.

6. The method as recited in claim 1, wherein the step of pre-processing the image data set calculates the one or more structure edges by determining a maximum absolute gradient for each voxel relative to the adjacent voxels.

7. The method as recited in claim 1, wherein pre-processing the image data set comprises partitioning the image data set into the plurality of sub-volumes.

8. The method as recited in claim 7, wherein the vascular structure is automatically determined based upon the differential processing applied to the plurality of sub-volumes.

9. The method as recited in claim 8, wherein differentially processing comprises implementing a fast algorithm in at least one sub-volume and a complex vessel tracking algorithm in at least one other sub-volume.

10. The method as recited in claim 1, wherein pre-processing the image data set comprises removing a portion of the image data set corresponding to a table.

11. The method as recited in claim 1, wherein generating the preliminary bone mask comprises classifying voxels as bone based on at least intensity.

12. The method as recited in claim 1, wherein automatically determining the vascular structure comprises applying at least one of a dynamic constrained region growing process, a bubble wave connectivity process, and a ray and contour propagation process.

13. The method as recited in claim 1, comprising the step of smoothing the vascular structure.

14. A computer program product comprising a computer readable media having a computer readable program code embodied therein, said computer readable program code adapted to be executed to implement a method for acquiring an image data set, the method comprising:
acquiring an image data set;
pre-processing the image data set to automatically calculate at least one or more seed points and one or more structure edges;
generating a preliminary bone mask to differentiate bone and vascular structures from the image data set, wherein the preliminary bone mask is generated for a plurality of sub-volumes comprising the image data set, each of the sub-volumes is identified based upon the degree of spatial separation between the bone and the vascular structures in the sub-volume, wherein differential processing to segment the bone and vascular structures is employed within each sub-volume based upon the spatial relationship between the bone and the vascular structures in the sub-volume;
automatically determining the vascular structure using the one or more seed points, the one or more structure edges, and the image data; and
subtracting the vascular structure from the preliminary bone mask to generate a bone mask.

15. The computer program as recited in claim 14, comprising a routine for subtracting the bone mask from the image data set to generate a bone-free volume data set.

16. The computer program as recited in claim 15, comprising a routine for rendering the bone-free volume data set to generate a bone-free volumetric rendering.

17. The computer program as recited in claim 14, wherein the routine for acquiring the image data set acquires a CTA data set of a head and neck region.

18. The computer program as recited in claim 14, wherein the routine for pre-processing the image data set calculates the one or more seed points using at least one of a geometric template and a functional template.

19. The computer program as recited in claim 14, wherein the routine for pre-processing the image data set calculates the one or more structure edges by determining a maximum absolute gradient for each voxel relative to the adjacent voxels.

20. The computer program as recited in claim 14, wherein the routine for pre-processing the image data set partitions the image data set into the plurality of sub-volumes.

21. The computer program as recited in claim 20, wherein the routine for automatically determining the vascular structure is based on the differential processing applied to the plurality of sub-volumes.

22. The computer program as recited in claim 21, wherein differentially processing comprises implementing a fast algorithm in at least one sub-volume and a complex vessel tracking algorithm in at least one other sub-volume.

23. The computer program as recited in claim 14, wherein the routine for pre-processing the image data set removes a portion of the image data set corresponding to a table.

24. The computer program as recited in claim 14, wherein the routine for generating the preliminary bone mask classifies voxels as bone based on at least intensity.

25. The computer program as recited in claim 14, wherein the routine for automatically determining the vascular structure applies at least one of a dynamic constrained region growing process, a bubble wave connectivity process, and a ray and contour propagation process.

26. The computer program as recited in claim 14, comprises a routine for smoothing the vascular structure.

27. A CT image analysis system, comprising:
an X-ray source configured to emit a stream of radiation;
a detector configured to detect the stream of radiation and to generate one or more signals responsive to the stream of radiation, wherein the detector comprises a plurality of detector elements;
a system controller configured to control the X-ray source and to acquire a set of image data from one or more of the detector elements via a data acquisition system; and
a computer system configured:
to receive the set of image data,
to pre-process the set of image data to automatically calculate at least one or more seed points and one or more structure edges,
to generate a preliminary bone mask to differentiate bone and vascular structures from the set of image data, wherein the preliminary bone mask is generated for a plurality of sub-volumes comprising the image data set, each of the sub-volumes is identified based upon a spatial relationship between the bone and the vascular structures in the sub-volume, and wherein differential processing to segment the bone and vascular structures is employed within each sub-volume based upon the spatial relationship between the bone and the vascular structures in the sub-volume;
to automatically determine the vascular structure using the one or more seed points, the one or more structure edges, and the set of image data, and
to subtract the vascular structure from the preliminary bone mask to generate a bone mask.

28. The CT image analysis system as recited in claim 27, wherein the computer system is configured to subtracting the bone mask from the set of image data to generate a bone-free volume data set.

29. The CT image analysis system as recited in claim 28, wherein the computer system is configured to render the bone-free volume data set to generate a bone-free volumetric rendering.

30. The CT image analysis system as recited in claim 27, wherein the computer system is configured to pre-process the set of image data by calculating the one or more seed points using at least one of a geometric template and a functional template.

31. The CT image analysis system as recited in claim 27, wherein the computer system is configured to pre-process the set of image data by calculating the one or more structure edges by determining a maximum absolute gradient for each voxel relative to the adjacent voxels.

32. The CT image analysis system as recited in claim 27, wherein the computer system is configured to pre-process the set of image data by partitioning the image data set into the plurality of sub-volumes.

33. The CT image analysis system as recited in claim 32, wherein the computer system is configured to automatically determine the vascular structure based on the differential processing applied to the plurality of sub-volumes.

34. The CT image analysis system as recited in claim 33, wherein differentially processing comprises implementing a fast algorithm in at least one sub-volume and a complex vessel tracking algorithm in at least one other sub-volume.

35. The CT image analysis system as recited in claim 27, wherein the computer system is configured to pre-process the set of image data by removing a portion of the image data set corresponding to a table.

36. The CT image analysis system as recited in claim 27, wherein the computer system is configured to generate the preliminary bone mask by classifying voxels as bone based on at least intensity.

37. The CT image analysis system as recited in claim 27, wherein the computer system is configured to automatically determine the vascular structure by applying at least one of a dynamic constrained region growing process, a bubble wave connectivity process, and a ray and contour propagation process.

38. The CT image analysis system as recited in claim 27, wherein the computer system is configured to smooth the vascular structure.

* * * * *

UNITED STATES PATENT AND TRADEMARK OFFICE
CERTIFICATE OF CORRECTION

PATENT NO. : 7,676,257 B2
APPLICATION NO. : 10/723192
DATED : March 9, 2010
INVENTOR(S) : Suryanarayanan et al.

It is certified that error appears in the above-identified patent and that said Letters Patent is hereby corrected as shown below:

In Column 6, Line 51, delete "and' structure" and insert -- and structure --, therefor.

In Column 11, Line 19, delete "used, for" and insert -- used for --, therefor.

In Column 12, Line 32, in Claim 1, after "sub-volume" delete "is".

Signed and Sealed this

Twenty-fifth Day of May, 2010

David J. Kappos
*Director of the United States Patent and Trademark Office*